(12) United States Patent
Ma et al.

(10) Patent No.: US 9,428,446 B2
(45) Date of Patent: Aug. 30, 2016

(54) PROCESS FOR THE PRODUCTION OF AMINOPROPYLMETHYLETHANOLAMINE

(75) Inventors: Yuhao Ma, Jiangsu (CN); Peijun Xu, Jiangsu (CN); Jieping Chen, Jiangsu (CN); Philippe Leconte, Saint Fons (FR); Ann Mu, Shanghai (CN)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 14/377,222

(22) PCT Filed: Feb. 10, 2012

(86) PCT No.: PCT/CN2012/071037
§ 371 (c)(1),
(2), (4) Date: Sep. 26, 2014

(87) PCT Pub. No.: WO2013/117013
PCT Pub. Date: Aug. 15, 2013

(65) Prior Publication Data
US 2015/0329479 A1    Nov. 19, 2015

(51) Int. Cl.
*C07C 253/30*    (2006.01)
*C07C 213/02*    (2006.01)

(52) U.S. Cl.
CPC ............ *C07C 253/30* (2013.01); *C07C 213/02* (2013.01)

(58) Field of Classification Search
CPC ........................... C07C 253/30; C07C 213/02
See application file for complete search history.

(56) References Cited

U.S. PATENT DOCUMENTS

| 5,734,069 A  * | 3/1998  | Toney ..................... | C11D 1/62 554/110 |
| 8,329,955 B2 * | 12/2012 | Letourneur ........... | C07C 209/48 564/490 |

FOREIGN PATENT DOCUMENTS

| CN | 1995009 A    | 7/2007  |
| CN | 101665440 A  | 3/2010  |
| EP | 0184408 A1   | 6/1986  |
| FR | 2921922 A1   | 10/2009 |
| JP | H 05246959 A | 9/1993  |

* cited by examiner

*Primary Examiner* — Shailendra Kumar
(74) *Attorney, Agent, or Firm* — Osha Liang LLP

(57) ABSTRACT

A new process for the production of APMMEA (aminopropylmethylethanolamine) is proposed. This process comprises at least 2 steps in which MEAPN (monomethylethanolaminopropionitrile) is first produced from MMEA (monomethylethanol amine) and ACN (acrylonitrile) and then said MEAPN is hydrogenated to obtain the corresponding amine, the APMMEA compound. APMMEA may be then eventually purified by several known process, notably by distillation.

11 Claims, No Drawings

PROCESS FOR THE PRODUCTION OF AMINOPROPYLMETHYLETHANOLAMINE

CROSS-REFERENCE TO RELATED APPLICATIONS

The present application is a U.S. national stage entry under 35 U.S.C. §371 of International Application No. PCT/CN2012/071037 filed Feb. 10, 2012, the whole content of this application being herein incorporated by reference for all purposes.

TECHNICAL FIELD OF THE INVENTION

The present invention relates to a process for the production of APMMEA (aminopropylmethylethanolamine).

BACKGROUND OF THE INVENTION

APMMEA is aminopropylmethylethanolamine or N-aminopropyl monomethylethanolamine (CAS Number: 41999-70-6)

MMEA is monomethylethanolamine, or N-Methylethanolamine (CAS Number:109-83-1)

ACN is acrylonitrile (CAS Number:107-13-1)

MEAPN is monomethylethanolaminopropionitrile (CAS Number: 34508-82-2)

APMMEA amine neutralizer is a clear, essentially colourless, low viscosity liquid, with a high flash point and a mild odour. It is miscible with water, alcohols, ethers and other solvents. The amine group of the compound can be used to neutralize carboxylic-functional polymers in order to solubilize them in water and to provide effective pH control of latex paints. The APMMEA amine neutralizer can also be used as a co-dispersant and as a wetting agent. Primary polymer resins in which the APMMEA amine neutralizer can be used include acrylics, alkyds and vinylics.

DESCRIPTION OF THE INVENTION

The present invention provides a new process for the production of APMMEA (aminopropylmethylethanolamine). This process comprises at least 2 steps in which MEAPN (monomethylethanolaminopropionitrile) is first produced from MMEA (monomethylethanolamine) and ACN (acrylonitrile) and then said MEAPN is hydrogenated to obtain the corresponding amine, the APMMEA compound. APMMEA may be then eventually purified by several known process, notably by distillation.

The present invention concerns a process for the production of APMMEA comprising at least 2 steps:
(a) Production of MEAPN from reaction of MMEA and ACN; and
(b) Hydrogenation of MEAPN to produce APMMEA.

Step (a)

This step (a) is a Michael reaction focused on the nucleophilic addition of an amine to an $\alpha,\beta$-unsaturated cyano compound.

Temperature of the reaction may be comprised between 30 and 100° C., preferably between 50 and 70° C. Reaction may be carried out at atmospheric pressure.

This step may be carried out without catalyst or specific solvent. Water can be used in the reaction medium.

During the reaction, molar/molar proportion of MMEA/ACN is preferably comprised between 0.98 to 1.2, more preferably comprised between 1.0 to 1.1, advantageously comprised between 1 and 1.02.

This step (a) may be conducted in any conventional equipment suitable to effect production of MEAPN. This step (a) may be carried out via a continuous or a discontinuous way. For example, suitable equipment includes a stirred tank or loop reactor.

Step (b)

One of the aims of the present invention is to provide a continuous or discontinuous process for the hydrogenation of a nitrile compound, MEAPN, to give the corresponding amine compound, APMMEA. This reaction notably occurs in the presence of a catalyst based on Raney metal in a medium comprising water in the presence of an inorganic base, preferably in the absence of solvent such as alcohol, which makes it possible to maintain a suitable catalytic activity in the reactor with a low consumption of catalyst per ton of amine compound produced.

To this end, the invention preferably provides a process for the manufacture of APMMEA by hydrogenation of MEAPN, which preferably consists in feeding a hydrogen gas and MEAPN to a reactor. The reaction medium may comprise a catalyst, notably suspended particles of catalyst based on Raney metal, an inorganic base and water.

The catalysts suitable for this step may be Raney metals, such as Raney nickel or Raney cobalt, preferably Raney nickel. Promoter elements can advantageously be used with the Raney metal. These promoter elements are chosen from the elements belonging to Groups IIB, and IVB to VIIB of the Period Table of the Elements. Advantageously, the promoter elements are chosen from the group consisting of titanium, chromium, zirconium, vanadium, molybdenum, manganese, cobalt, nickel, zinc, iron and their combinations.

Catalyst may be subjected to a regeneration process before being recycled to the reaction medium. The said regeneration process may comprise a stage of washing the catalyst with water in order to remove most of the organic compounds, the washed catalyst being subjected to treatment with a base and/or under hydrogen pressure, followed by washing with an aqueous alkali metal hydroxide solution and/or water.

According to a preferred object of the invention, the hydrogenation reaction is carried out in the presence of a solvent advantageously composed of the amine obtained by the hydrogenation, ie. APMMEA. The concentration of APMMEA in the reaction medium is advantageously between 50% and 99% by weight, preferably between 60 and 99% by weight, of the liquid phase of the hydrogenation reaction medium.

The hydrogenation reaction may be carried out in the presence of water as other component of the reaction medium. This water is generally present in an amount of less than or equal to 50% by weight, advantageously of less than or equal to 20% by weight, in the liquid phase of the total reaction medium and more preferably still between 0.1% and 15% by weight.

The hydrogenation reaction is carried out in the presence of an inorganic base, such as LiOH, NaOH, KOH, RbOH, CsOH and/or their mixtures. NaOH and KOH are preferably used.

The amount of base added may be determined in order to have at least 0.2 mol of base per kilogram of catalyst, preferably between 0.2 and 5 mol of base per kg of catalyst, and more advantageously still between 1 and 3 mol of base per kg of catalyst.

The hydrogenation reaction may be carried out at a temperature of less than or equal to 150° C., preferably of less than or equal to 120° C. and more preferably still of less than or equal to 100° C. The reaction temperature is generally between 50° C. and 100° C. The hydrogen pressure in the reactor can be between 0.10 and 10 MPa approximately.

The hydrogenation step can be conducted in any conventional hydrogenation equipment suitable to effect conversion. For example, suitable equipment includes a stirred tank or loop reactor, a continuous stirred tank reactor, a continuous gas lift reactor, a fixed-bed reactor, a trickle-bed reactor, a sieve-tray reactor or a reactor permitting a cross-flow filtration. According to an other embodiment of the invention, the hydrogenation reaction of the invention is carried out continuously in an apparatus or device described in FR2921922. The apparatus suitable for the implementation of the process of the invention makes it possible to produce excellent gas/liquid contact, rapid and efficient separation of these two phases after contact, continuous separation of the hydrogenate and of the catalyst and the recycling of the latter, in a time compatible with the least possible deactivation of the said catalyst.

Further to step (b), APMMEA may be eventually purified by several known process, notably by distillation, in a step (c). This purification may be done in a continuous or in a batch way. Such a distillation can be carried out at atmospheric pressure or under reduced pressure.

The invention will be illustrated below with the aid of examples.

EXPERIMENTAL PART

Example 1

Step (a)

To a 500 ml round bottomed flask fitted with a mechanical stirrer, thermometer and pressure-equalizing dropping funnel, reflux condenser was added 180 g of monomethylethanolamine (MMEA). The dropping funnel was charged with 106 g of acrylonitrile. Acrylonitrile (ACN) was added with stirring at a rate that kept the reaction temperature from rising over 50° C., after the addition the reaction was allowed to proceed for an additional 2 hours at 50° C., At a conversion of 99%, monomethylethanolaminopropionitrile (MEAPN) was formed with a selectivity of 100%.

Example 2

Step (a)

To a 500 ml round bottomed flask fitted with a mechanical stirrer, thermometer and pressure-equalizing dropping funnel, reflux condenser was added 180 g of monomethylethanolamine (MMEA) with 10.8 g of water. The dropping funnel was charged with 127.2 g of acrylonitrile. Acrylonitrile (ACN) was added with stirring at a rate that kept the reaction temperature from rising over 60° C., after the addition the reaction was allowed to proceed for an additional 2 hours at 60° C., At a conversion of 99%, monomethylethanolaminopropionitrile (MEAPN) was formed with a selectivity of 100%.

Example 3

Step (b)

260 g of APMMEA as solvent, 17 g of water and 7.5 g Raney nickel doped with chromium were charged to a stirred reactor. 0.45 g of NaOH were added in order to obtain a NaOH/Ni ratio of 1.5 mol/kg. The mixture was kept stirred at a temperature of 80° C. and 25 bar hydrogen pressure. 160 g of MEAPN were added to the reactor in 2 hours. Left reaction go to zero H2 consumption. At a conversion of 100%, APMMEA was formed with a selectivity of 99%.

Example 4

Step (b)

260 g of APMMEA as solvent, 17 g of water and 7.5 g Raney nickel doped with chromium were charged to a stirred reactor. 0.9 g of NaOH were added in order to obtain a NaOH/Ni ratio of 3 mol/kg. The mixture was kept stirred at a temperature of 80° C. and 25 bar hydrogen pressure 160 g of MEAPN were added to the reactor in 2 hours. Left reaction go to zero H2 consumption.

At a conversion of 100%, APMMEA was formed with a selectivity of 98.5%.

What is claimed is:

1. A process for the production of APMMEA comprising at least 2 steps:
    (a) Production of MEAPN from reaction of MMEA and ACN;
    (b) Hydrogenation of said MEAPN in the presence of a reaction medium comprising a catalyst, inorganic base, and water to produce APMMEA; and
    (c) Isolation of said APMMEA.
2. The process according to claim 1, wherein in said step (a) the molar/molar proportion of said MMEA/ACN is comprised between 0.98 and 1.2.
3. The process according to claim 1, wherein the catalyst is a Raney metal.
4. The process according to claim 1, wherein said inorganic base is selected from the group consisting of LiOH, NaOH, KOH, RbOH, CsOH and their mixtures.
5. The process according to claim 1, wherein the amount of said inorganic base added is determined in order to have at least 0.2 mol of base per kilogram of said catalyst.
6. The process according to claim 1, wherein in said step (b) the hydrogenation reaction is carried out in the presence of said APMMEA as solvent.
7. The process according to claim 6, wherein the concentration of said APMMEA in the reaction medium is advantageously between 50% and 99% by weight, of the liquid phase of the hydrogenation reaction medium.
8. The process according to claim 1, wherein in said step (b) the hydrogenation reaction is carried out in the presence of water as other component of the reaction medium.
9. The process according to claim 8, wherein the water is present in an amount of less than or equal to 50% by weight, in the liquid phase of the total reaction medium.
10. The process according to claim 8, wherein the water is present in an amount comprised between 0.1 and 15% by weight, in the liquid phase of the total reaction medium.
11. The process according to claim 1, wherein said APMMEA is purified by continuous or batch distillation in a step (c) at atmospheric or reduced pressure.

* * * * *